US00PP08450P

United States Patent [19]

Zaiger et al.

[11] Patent Number: Plant 8,450

[45] Date of Patent: Nov. 9, 1993

[54] NECTARINE TREE "ARCTIC PRIDE"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 4,140

[22] Filed: Jan. 11, 1993

[51] Int. Cl.[5] ..... A01H 5/00

[52] U.S. Cl. ..... Plt./40.1

[58] Field of Search ..... Plt./40.1

*Primary Examiner*—James R. Feyrer

[57] ABSTRACT

A new and distinct variety of nectarine tree which has the following unique combination of features that are desirable in a new variety:

1. Heavy and regular production of fruit.
2. Fruit with excellent flavor and eating quality.
3. Fruit with firm white flesh having good handling, storage and shipping quality.
4. Fruit having a high degree of soluble solids, (14.8 Brix).
5. Fruit ripening in the late maturity season.
6. Relatively uniform maturity of large, freestone fruit.
7. Having a vigorous, upright growth habit.

1 Drawing Sheet

ORIGIN OF THE VARIETY

Our new and distinct nectarine variety was originated by us in our experimental orchard located near Modesto, Calif. as a third generation seedling from a cross between two selected seedlings with the field identification numbers of 21GA1110 and 32EA260. The seedling 21GA1110, which is the female parent originated from a cross between Ruby Gold Nectarine (U.S. Plant Pat. No. 3,101) and Redwing Peach (U.S. Plant Pat. No. 621) and the pollen parent with the identification number of 32EA260 originated from a cross between O'-Henry Peach (U.S. Plant Pat. No. 2,964) and Giant Babcock Peach (U.S. Plant Pat. No. 1,353). A large group of these third generation seedlings were grown and maintained under close observation, one such late maturing seedling, which is the present variety, having especially desirable fruit characteristics was selected for asexual reproduction and commercialization.

ASEXUAL REPRODUCTION OF THE VARIETY

Asexual reproduction of our new and distinct variety was performed by budding in our experimental orchard located near Modesto, Calif. and shows that such reproduction run true to the original tree and all characteristics are established and transmitted through succeeding propagations.

SUMMARY OF THE VARIETY

The present new and distinct variety of nectarine tree is of large, vigorous, upright growth and a regular and productive bearer of large, firm, white flesh, freestone fruit with excellent flavor and eating quality. The fruit is further characterized by being relatively uniform in maturity, having good handling and shipping quality, a high degree of attractive red skin color and ripening in the late maturity season.

DESCRIPTION OF THE PHOTOGRAPHS

The accompanying photographic reproductions in color are typical specimens of the foliage and fruit of our new nectarine variety. The illustrations show the upper and lower surface of the leaves, an exterior and sectional view of a fruit divided in the suture plane to reveal flesh coloration and a stone remaining in place. The photographic illustrations were taken shortly after being picked at maturity (firm ripe) and the colors are as nearly true as is reasonably possible in a color representation of this type.

DESCRIPTION OF THE VARIETY

The following is a detailed botanical description of the new variety of nectarine tree, its flowers, foliage and fruit as based on observations of the specimen grown near Modesto, Calif., with color terminology (except those in common terms) in referenced to Reinhold Color Atlas by A. Kornerup and J. H. Wanscher.

Tree:

*Size.*—Large.
*Vigor.*—Vigorous.
*Growth.*—Upright.
*Density.*—Medium dense.
*Bearing.*—Regular.
*Production.*—Productive.

Trunk:

*Size.*—Medium.
*Texture.*—Medium shaggy.
*Color.*—Grayish brown to brown (5-E-6) to (5-E-7).

Branches:

*Size.*—Medium.
*Surface.*—Smooth to medium rough.
*Lenticels.*—Numerous. Medium to large size.
*Color.*—Light brown to brown.

Leaves:

*Size.*—Large. Average length — 6". Average width — 1⅝".
*Form.*—Lanceolate. Pointed.
*Margin.*—Crenate.
*Texture.*—Smooth.
*Thickness.*—Medium.
*Petiole.*—Medium length. Medium thickness.
*Glands.*—Number varies from 1 to 4. Average number 2. Reinform. Positioned on upper portion of petiole and lower portion of leaf blade.
*Color.*—Upper surface — green to dark green (26-F-5) to (26-F-8). Lower surface — dull green to grayish green (26-D-5) to (26-D-6).

Flower buds:

*Size.*—Medium to large.
*Length.*—Medium.
*Form.*—Plump.

Flowers:

*Size.*—Large — showy.
*Blooming period.*—Date of first bloom Mar. 4, 1991. Date of full bloom Mar. 11, 1991. Varies slightly with climatic conditions.
*Pollen.*—Present.
*Color.*—Pink.

Fruit:

*Maturity when described.*—Firm ripe.
*Date of first picking.*—Aug. 26, 1991.
*Date of last picking.*—Aug. 29, 1991.
*Size.*—Large — comparatively uniform. Average diameter axially 2⅞" to 3¼". Average transversely in suture plane 3" to 3¼".
*Form.*—Nearly globose. Slightly flattened at stem. Slight apical tip.
*Suture.*—Shallow — nearly rounded. Extends from base to just beyond apex.
*Ventral Surface.*—Nearly rounded — only very slightly lipped.
*Cavity.*—Nearly rounded — slightly elongated in suture plane. Average depth — ½". Average breadth — ⅝".
*Base.*—Retuse.
*Apex.*—Slight pistil point, usually slightly more pronounced on one side.

Flesh:

*Ripens.*—Evenly.
*Texture.*—Firm.
*Juice.*—Moderate.
*Flavor.*—Excellent — sweet, mild, subacid.
*Eating quality.*—Excellent.
*Amygdalin.*—Undetected.
*Fibers.*—Few, small, tender.
*Aroma.*—Moderate.
*Color.*—White to pinkish white (7-A-1) to (7-A-2). Pit cavity rose red to red (12-A-7) to (12-B-8). Red streaks bleeding into flesh from pit cavity.

Skin:

*Thickness.*—Medium.
*Texture.*—Medium — tenacious to flesh.
*Tendency to crack.*—Very slight.
*Down.*—Wanting.
*Color.*—Ground color, white to pinkish white (12-A-1) to (12-A-2). Overspread with red to madder red (11-A-6) to (11-B-8).

Stone:

*Type.*—Freestone. Varies from full freestone to small fibers attached to some stones.
*Size.*—Large. Average length 1½". Average breadth 1⅛". Average thickness ½".
*Form.*—Usually obovate. Varies from ovate to obovate.
*Base.*—Varies from straight to slightly rounded.
*Apex.*—Acuminate.
*Surface.*—Irregularly furrowed toward apex, pitted throughout, heavier toward base.
*Sides.*—Equal to unequal.
*Tendency to Split.*—None.
*Color.*—Brown to reddish brown (9-E-6) to (9-D-6).

Use: Dessert.
*Market.*—Local and long distance.
Keeping quality: Good.
Shipping quality: Good.

The present new variety of nectarine tree, its flowers, foliage and fruit herein described may vary in slight detail due to climatic, soil conditions and cultural practices under which the variety may be grown. The present description is that of the variety grown under the ecological conditions prevailing near Modesto, Calif.

We claim:

1. A new and distinct variety of nectarine tree, substantially as illustrated and described, characterized by its large size, vigorous upright growth and being a productive and regular bearer of large, white flesh, freestone fruit with excellent flavor and eating quality; the fruit is further characterized by having firm flesh with good handling and shipping quality, relatively uniform ripening throughout the tree, having a high degree of soluble solids (14.8 brix) and maturing in the late season with an attractive red skin color.

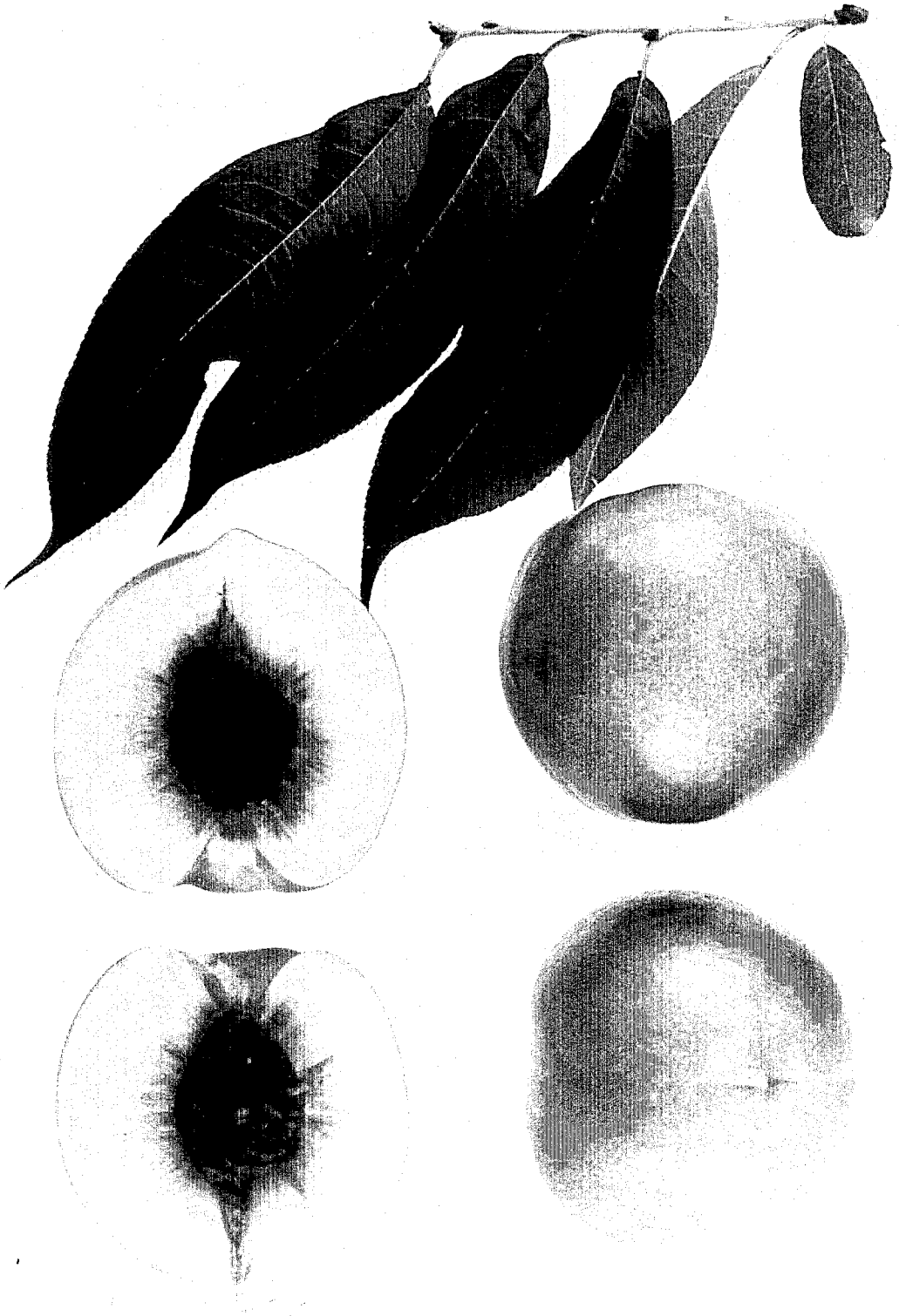

* * * * *